United States Patent [19]

Claessens

[11] Patent Number: 6,102,873
[45] Date of Patent: Aug. 15, 2000

[54] IDENTIFICATION OF STIMULI

[75] Inventor: Dominique Paul Gerard Claessens, Geneva, Switzerland

[73] Assignee: Eyelight Research N.V., Curacao, Netherlands

[21] Appl. No.: 09/155,055

[22] PCT Filed: Apr. 14, 1996

[86] PCT No.: PCT/NL97/00187

§ 371 Date: Sep. 23, 1998

§ 102(e) Date: Sep. 23, 1998

[87] PCT Pub. No.: WO97/38623

PCT Pub. Date: Oct. 23, 1997

[30] Foreign Application Priority Data

Apr. 12, 1996 [NL] Netherlands .......................... 1002853

[51] Int. Cl.⁷ ...................................................... A61B 5/00
[52] U.S. Cl. ........................................... 600/595; 600/558
[58] Field of Search .................................. 600/558, 587, 600/595; 364/413.01

[56] References Cited

U.S. PATENT DOCUMENTS 3,388,630  6/1968  Leitner .
4,894,777  1/1990  Negishi ................................... 364/419
4,992,867  2/1991  Weinblatt ............................... 358/108

FOREIGN PATENT DOCUMENTS

| 0 125 808 | 11/1984 | European Pat. Off. . |
| 0 305 124 | 3/1989 | European Pat. Off. . |
| 9403971 | 5/1994 | Germany . |
| 1022661 | 3/1966 | United Kingdom . |
| 2 232 248 | 12/1990 | United Kingdom . |
| 90 02453 | 3/1990 | WIPO . |
| 9 2 08202 | 5/1992 | WIPO . |

*Primary Examiner*—Max Hindenburg
*Attorney, Agent, or Firm*—Foley & Lardner

[57] ABSTRACT

Method and device for identification of stimuli, in which one or various identification methods in combination can be applied. Here, stimuli in their original manifestation, as well as stimuli positions and orientations are determined and it is ascertained which stimuli respondents have in their field of vision, from which moment, for how long and under which circumstances, as well as the way in which they handle and manipulate them.

15 Claims, No Drawings

IDENTIFICATION OF STIMULI

BACKGROUND OF THE INVENTION

The invention relates to a method and device for identification of stimuli. Such a method is described in NL-A-1002854, which was filed simultaneously with the present application.

SUMMARY OF THE INVENTION

In this method, the intention is to identify stimuli as well as stimuli positions and orientations. The error margin in this method is partly connected to the comparison algorithm applied for said identification, as well as to the determination of the instances of measurement.

A method of identifying objects comprising: measuring at least a first characteristic property in each of a first plurality of different views an object and obtaining a first set of signals representative thereof; storing the first set of signals as a reference; measuring the first characteristic property in each of a second plurality of views of the object as it is manipulated and obtaining a second set of signals representative thereof; measuring the time period during which each of a plurality of the second plurality of views is present; comparing the second set of signals to the first set of signals; and determining from the comparison which of the views of the first plurality of different views of the object occurred during the manipulation and the time period of occurrence of at least one of the views.

The object of the invention is to provide a different method by which the correct identification can be realized in nearly all cases. Such a method according to the invention is characterized in that one or more different methods of identification can be applied in combination. Methods each having their specific advantages and disadvantages, together yielding a smaller error margin than each on its own.

Further, the method according to the invention is characterized in that a flexible measuring frequency is employed, in which the instance of measuring can be made dependent of conditions. Further, the method according to the invention is characterized in that measuring sensors, being part of the device, not only record an image of a stimulus once every instance of measurement, but at the same record semi-continuous stimuli data, so as to immediately and/or afterwards select the data best suitable to be used for stimuli identification.

Furthermore, the method according to the invention is characterized in that contours of the stimuli to be identified are determined and are divided in segments which are applied for determining the positions, movements, rotations, orientations and/or distortions of the stimuli. Further, the method is characterized in that the possible identifications determined by the various algorithms together, including the most likely one, are additionally checked by way of a series of conditions relating to logical connections. The final identification concerns the stimulus having the highest position in a probability value order at the same time meeting at least one established part of the tested conditions.

The stimuli that can be determined practically error-free, concern printed matter, illustrations, photos, texts, instructions, manuals, etc., in printed media, including magazines, dailies, specialist journals, brochures, flyers, free local printed matter, DM-material, books, guides, etc. Yet also products, product components, product concepts, models, e.g. of cars, and designs, as well as packages and other three-dimensional objects.

The method according to the invention concerns a stimuli classification and read in method, which detects any variant of stimuli exposure beforehand and stores it in such a way, that comparison with a read-in stimulus enables an error-free recognition within a short time, e.g. within one second, as well as an error-free determination of position and orientation of the read-in stimulus. In this way, it is possible to detect e.g. manipulations of stimuli by respondents, such as with printed matter, the way of holding it and/or flipping the pages. Yet also the handling and manipulation of objects, e.g. turning objects for the purpose of observing it at various viewing angles.

Recognizing stimuli requires previous read in and as a consequence of this, knowledge of stimuli characteristics and subsequently, on the basis of comparison methods and algorithms, recognizing of stimuli presented for identification.

With the method according to the invention in particular, several different methods, each having their specific advantages and disadvantages, are applied in combination, together resulting in a smaller error margin than each on its own. To that end, the combination of said methods is such, that the disadvantages of the individual methods are compensated, whereas the advantages are combined.

Recognizing objects in 3 dimensions is based on the same method in which characteristics of each variant of exposure are read in beforehand.

The device according to the method consists of one or more sensors by which characterizing properties of stimuli of a stimulus in its entirety and on partly non-visible stimuli, including partly covered stimuli. For example, a partly opened magazine or daily will already sufficient to be able to determine the position, orientation and the number of that specific page with certainty. Rotations up to 180° are tolerated. One or some parts of 3-dimensional objects, exposed completely or partly during manipulation, will be sufficient for identification of said objects. The method according to the invention is an indispensable part in the chain of activities by means of which the massive measurement of respondent reactions to massive amounts of stimuli, and parts of stimuli, can be executed.

In a general sense, said method can be applied to many types of stimuli, such as previously mentioned and specified, including 3-dimensional objects, yet also to the identification of characteristics of human beings and animals, such as e.g. faces and postures, also with facial decorations changed by time, such as glasses, moustache and hair, not by applying a most critical identification standard, but by a standard relating to the data lying underneath. The method is also applicable for identification of movements and characteristics of dynamic actions, e.g. movements of human beings and animals, including natural movements and facial expression; but also for mechanically produced dynamics, such as movements of apparatus and actions of robots. The thus obtainable data can be applied e.g. for the benefit ergonomic analyses.

The method according to the invention can further be applied with all projects, whether or not industrial, where a quick identification of objects, place and orientation is desired, e.g. with automated production.

By way of example, a method, which can be followed together with the method and the system according to the invention for identification of stimuli and determination of the positions and orientations of said stimuli, will now be indicated step by step. For the sake of clarity, the steps in the example are illustrated by way of printed matter stimuli in the form of pages as those of a magazine.

Reading in images, and producing characteristics, of several views on a three-dimensional object can e.g. be regarded as a ranking of stimuli, such as e.g. the pictures of films, or, for the example given below, as the various pages of a magazine.

Steps with Reading in Reference Stimuli Beforehand and Producing the Accompanying Characteristics:

1. Positioning said stimuli on a presentation surface such as placing a magazine in a fixed position on a reading table.

2. Leafing through said magazine page by page, in which each page is read in as an individual stimulus and is subsequently recorded and classified, its characteristics being stored in such a way, that later comparison to that of a stimulus to be identified is possible within a short time, e.g. within one second.

Steps with semi-continuous Recording of Images and Producing the Characteristics of Stimuli to be Identified:

After reading in the characteristics of the identification stimuli beforehand, e.g. respondents are given the opportunity to leaf through the "learned" magazine. This can be done page by page, from beginning to end, but e.g. also arbitrarily, depending on the preferences and interests of respondents.

3. Semi-continuous recording of images and subsequent storage in a buffer having a storage capacity of e.g. a few hundred images with a total time of e.g. a number of seconds. The buffer has a cyclic structure, for example: it always contains the most recently recorded images. When the full capacity is used, the "oldest" image is removed from the buffer and the "latest", most recent image is added to the buffer.

4. Per time interval, e.g. shorter than the buffer time, directly and/or afterwards selecting from the semi-continuous recorded images the image best suitable for use in stimuli identification. On the basis of the extent of the image information and the quality of said information for identification, for example.

With other methods, e.g. one image per page is recorded in an instance which e.g. is determined by a preset measuring frequency. Such methods do not take into account the individual leafing behaviour of respondents. For example, if e.g. a page is not released, and as a result may be moving continuously, an image could be "moved", to such an extent that the image information will not be suitable for identification purposes.

However, with the method according to the invention, semi-continuous recordings of the same pages are made e.g. as long as they are lying open. From the recorded images, directly and/or e.g. per buffer time, one determines the most suitable image, by means of which the identification will be executed.

The best image is selected directly and/or per buffer time. Identification takes place on all thus selected images. Several of these images can relate to one and the same stimulus, stimulus view and/or parts of it to be identified.

In addition, the starting time at which the pages are opened is determined accurately, as well as the length of time during which said pages remain opened and the stimuli can thus be visible for respondents.

Depending on whether or not a, e.g. predetermined, maximum time to be spent, e.g. per stimulus, per page, per double page or per magazine, a signal can be produced by a means of a signalling device, e.g. a loudspeaker. For example, for leafing further, or, generally, handling another object.

5. Determining the contours of an object per image, e.g. on the basis of density value transitions. For an opened magazine this means: determining the outer contour of e.g. the opened double page.

6. Dividing the contours into segments.

7. Determining the location, movements and transformation of each of the segments from subsequent semi-continuous images recorded by the sensors.

Here, among other things, the segments play the role of "movement detectors" and are situated with reason along the contour of the magazine. After all, on turning a page, it can already be moving at the edge, whereas the middle of the page is still. Therefore, movement detection preferably takes place at the edge of the magazine.

From the shape of the segments, it can be deducted if pages are lying open; from the transformations it can be deducted if, and to what extent, pages are partly covered, and also if, and in what direction, pages are turned.

8. Determining the position, rotation, orientation of the pages and with that of the magazine, on the basis of the geometry of said segments. The method according to the invention is characterized in that before the image contents are involved in the actual identification, the stimulus position, rotation and orientation are always determined accurately.

Steps for the Purpose of identification of Stimuli

9. Selecting the available stimuli previously stored for identification, on the basis of the geometry of the contour segments of the stimulus read-in.

10. Dividing the visible part of the pages being within the contours into one or more planes, such as rectangles, polygons or circles, including concentric circles, e.g. with identical surfaces. For example, 9 planes per page, 18 planes for the double page. Determining the monochrome density value characteristics per plane. For example, the average, minimum, maximum and/or most frequent density value, e.g. a distribution, including a histogram distribution, of the monochrome density values present in the reading image.

For a double page divided in 18 planes, this yields 18 times a ranking of comparison values.

If the rankings are spectrally divided and are individually composed, e.g. for the colours red, green and blue, this yields 3×18=54 rankings of spectral density comparison values.

12. Comparing the comparison values of the stimulus to be identified with the predetermined comparison values of the identification stimuli available for comparison.

In the comparisons, individual and respective values are compared to each other and the numerical differences thereof are determined. The numerical differences are summated, resulting in the "error value" of the stimulus to be identified with one of the reference stimuli.

Thus, said stimulus to be identified is compared with all reference stimuli.

13. Ranking according to probability values on the basis of the ranking of "error values" determined from the above. The smallest error value occupies the highest position in the ranking. This concerns the page which according to said comparison method is the most likely to correspond to (resembles the most) the page to be identified.

The greatest error value occupies the lowermost position in the ranking. This is the page which is the least likely to correspond to the page to be identified.

14. Said probability value ranking concerns the partial result according to the density value comparison algorithm.

Due to the fact that the comparison method is based on density values, e.g. a white and a black page will not in the least resemble each other. However, a uniformly grey page and a text page can resemble each other in the case that e.g.

the average density of the text page corresponds to that of the uniformly grey page.

In order to eliminate the algorithm-connected disadvantages of comparison methods, with the method according to the invention it is possible to apply different methods and algorithms in a certain combination with each other.

Thus, in addition to said method based on monochrome and/or spectral densities, one also applies methods based on monochrome and/or spectral density transitions, expressed in image frequencies, as well as methods based on monochrome and/or spectral density transition directional distributions.

Densities can be connected with irradiating the stimuli through optical irradiation sources, such as visible light sources, infrared and ultraviolet sources, etc., but also with irradiation through any other type of irradiation source, including ultrasound, radar, and X-ray.

According to methods based on density transition values, a uniformly grey page and a text page will not resemble each other. After all, in case of the text page, there are many abrupt black and white transitions. In case of a uniformly grey page, there are no transitions at all.

15. Determining per plane the characteristics of the image frequencies, e.g. the minimum, maximum and/or most frequently occurring density transition value, e.g. a distribution, including a histogram distribution, of the image frequencies present in the recorded image.

For a double page divided in 18 planes, this produces 18 times a ranking of comparison values for this method too. If the rankings are spectrally separated and are separately composed, e.g. for the colours red, green and blue, this produces 3×18=54 rankings of comparison values.

16. Comparing the comparison values of the stimulus to be identified to the predetermined comparison values of the identification stimuli available for comparison.

With the comparisons, the respective individual values are compared to each other and the numerical difference thereof is determined. The differences are summated, which again results in an "error value" of the stimulus to be identified with one of the reference stimuli.

Thus, the stimulus to be identified is compared to all reference stimuli.

17. Classify according to probability value on the basis of the ranking of "error values" determined from the above.

18. This classification of probability values concerns the partial result of the density transition value comparison algorithm.

19. Comparing the respective first, second, third, etc. selections according to the various algorithms and determining the composite error values. This is the sum of the error values of one and the same identification for each of the individual methods.

20. Classifying the composite error values.

The result of the classification of the composite error values can be such that the page having the smallest composite error value, i.e. the top position in the final classification and with that the page which according to the combination of each of the comparison methods applied is the most likely to correspond to the page to be identified, does not result in the smallest error value with each of the comparison methods, but takes up the second, third, or another position in the classification. The reverse is also possible: the result of the classification of the error values of the individual comparison methods can be such that a specific page will hardly ever result in the smallest error value, but will always take up a second or third position in the classification, whereas that page will result in the smallest composite error value, i.e. takes up the top position in the final classification and with that the page which according to the combination of each of the comparison methods applied is the most likely to correspond to the page to be identified. ps The smallest composite error value takes up the highest position in said final classification. This concerns the page which according to the combination of each of the comparison methods applied is the most likely to correspond to the page to be identified.

21. Testing the most likely identification by logical connections.

For example, is the number of the identified page in ranking with the previous and following page numbers? After all, on leafing through a magazine from beginning to end, the subsequent pages will generally show increasing page numbers.

For example, was the number of the identified page still missing in the ranking of identified pages? Or had the most likely page already been identified once or several times, i.e., turned up once or several times by the same respondent, etc.

For example, is the page identification specific? That is, is the difference in composite error values of the page having the highest final classification big in relation to that of the page having the second highest final classification, etc.

The order of leafing, leafing further and leafing back, can be determined e.g. by the way in which the contour segments between consecutive images move. In doing so, one can obtain one or more logical connections from a ranking of images as well, which will have to correspond to the identification result to a certain extent.

When, e.g. in the case of 3 conditions, two out of the three conditions can be confirmed positively, the most likely page identification according to the method will be confirmed positively too. However, if two out of the three conditions should be confirmed negatively, the most likely page identification will be rejected.

22. Determining whether the most likely identification is able to confirm at least a part, e.g. half or two thirds, of the number of conditions to be tested, as being positive.

23. In the case where the most likely identification is able to confirm at at least a part of the number of conditions to be tested, as being positive, said most likely identification counts as the overall identification result. If the determined part of the conditions which should be confirmed positively is not made, the conditions will be tested by the second most likely identification, which, as described above, can be the most likely identification of one of the individual comparison methods, and after that the third most likely identification, etc., for determining the overall identification result.

If the composite error values are unusually large and none of the likely identifications makes the determined part of the conditions that must be confirmed positively, the system according to the invention indicates that the identification can not be executed.

The method described above not only enables very accurate identifications to be made, but also provides specificity values and certainty values, by which the method intrinsically has a means of indicating how recognizable a stimulus is and how certain an identification is. With the method described above, an error margin of better than 1% can be realized.

It will be obvious, that in the above the invention has only been explained by way of some specific examples, as regards to the method, the equipment used with it, the applications and the possible result of measurements, and that many changes and/or additions can be made without leaving the inventive idea.

What is claimed is:

1. A method of identifying objects comprising;
measuring at least a first characteristic property in each of a first plurality of different views of an object and obtaining a first set of signals representative thereof;
storing said first set of signals as a reference;
measuring said first characteristic property in each of a second plurality of views of said object as it is manipulated and obtaining a second set of signals representative thereof;
measuring the time period during which each of a plurality of said second plurality of views is present;
comparing said second set of signals to said first set of signals; and
determining from said comparison which of said views of said first plurality of different views of said object occurred during said manipulation and the time period of occurrence of at least one of said views.

2. The method of claim 1, wherein said steps of measuring said first characteristic property comprise;
irradiating said object and;
measuring the response to said irradiating.

3. The method of claim 2, wherein said step of irradiating is conducted with a radiation source with a range of radiation selected from at least one from the group of visible, infrared, ultraviolet, ultrasound, radar and x-ray.

4. The method of claim 1, wherein said first characteristic property is selected from one from the group of monochrome spectral density, monochrome spectral density transitions, monochrome density distributions, monochrome contours, color spectral density, color spectral density transitions, color density distributions or color contours.

5. The method of claim 4, wherein said method is repeated for a second characteristic property.

6. The method of claim 1, further comprising calculating an error value for each of a plurality of said second plurality of different views relative to said first plurality of different views.

7. The method of claim 6, further comprising;
determining probability values of identification of views based on said error values and;
ranking said probability values of identification.

8. The method of claim 4, further comprising dividing contours of said views of said object into segments.

9. The method of claim 8, further comprising applying said segments for determining at least one of position, movement, rotation, orientation or distortion of said object.

10. The method of claim 1, wherein said signals are measured and recorded semi-continuously in a buffer.

11. The method of claim 10, further comprising selecting the signal best suitable for identifying views of said object.

12. The method of claim 11, wherein movements and dynamic actions of human beings, animals, mechanisms or apparatus are identified using said method.

13. The method of claim 11, wherein the step of measuring comprises employing a flexible frequency.

14. The method of claim 11, wherein the step of comparing further comprises testing by conditions relating to logical connections.

15. The method of claim 11, wherein said object is printed matter including a plurality of pages, with a plurality of said pages comprising said different views of said object, and wherein said first characteristic property is measured for a plurality of said pages during said measuring steps.

* * * * *